United States Patent
Nova et al.

(10) Patent No.: US 6,965,799 B2
(45) Date of Patent: Nov. 15, 2005

(54) THERAPY AND MONITORING ELECTRODES WITH PATIENT ACCOMMODATING FEATURES

(75) Inventors: Richard C. Nova, Kirkland, WA (US); Kevin K. Covey, Marysville, WA (US); Joseph L. Sullivan, Kirkland, WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 276 days.

(21) Appl. No.: 10/094,949

(22) Filed: Mar. 8, 2002

(65) Prior Publication Data

US 2003/0171797 A1 Sep. 11, 2003

(51) Int. Cl.[7] .................................................. A61N 1/04
(52) U.S. Cl. ........................ 607/142; 607/148; 607/152
(58) Field of Search .......................... 607/142, 148, 607/149, 152, 2, 4–9; 600/372, 391–393; 206/727, 390; D24/187

(56) References Cited

U.S. PATENT DOCUMENTS

| | | | | |
|---|---|---|---|---|
| 711,981 | A | * 10/1902 | Lankenau | ................... 206/390 |
| 4,034,854 | A | * 7/1977 | Bevilacqua | ................. 206/370 |
| 4,353,373 | A | * 10/1982 | Sessions et al. | ............ 600/392 |
| 4,543,958 | A | * 10/1985 | Cartmell | ..................... 600/391 |
| 4,850,356 | A | * 7/1989 | Heath | ......................... 607/142 |
| 4,934,383 | A | * 6/1990 | Glumac | ....................... 607/152 |
| 5,255,677 | A | * 10/1993 | Schaefer et al. | ............ 600/384 |
| 5,366,497 | A | * 11/1994 | Ilvento et al. | .............. 607/142 |
| 5,674,253 | A | 10/1997 | Adams et al. | |
| 5,817,151 | A | 10/1998 | Olson et al. | |
| 5,824,033 | A | * 10/1998 | Ferrari | ........................ 607/142 |
| 5,919,155 | A | * 7/1999 | Lattin et al. | .................. 604/20 |
| 5,984,102 | A | * 11/1999 | Tay | ............................. 206/701 |
| 6,101,413 | A | 8/2000 | Olson et al. | |
| 6,115,638 | A | * 9/2000 | Groenke | ...................... 607/142 |
| 6,125,298 | A | 9/2000 | Olson et al. | |
| 6,134,468 | A | 10/2000 | Morgan et al. | |
| 6,240,323 | B1 | * 5/2001 | Calenzo et al. | ............. 607/142 |
| 6,714,824 | B1 | * 3/2004 | Ohta et al. | ................... 607/142 |

* cited by examiner

*Primary Examiner*—Jeffrey R. Jastrzab
(74) *Attorney, Agent, or Firm*—Ingrassia Fisher & Lorenz PC

(57) ABSTRACT

Medical electrode arrangements are provided for electrotherapy and monitoring applications. In one embodiment, each electrode arrangement includes a smaller electrode that is releasably attached to the back of a larger electrode. For adult applications, the larger electrode is applied to the patient. For pediatric applications, the larger electrode is preferably removed, and the smaller electrode is applied to the patient. Face-to-face and back-to-back electrode arrangement configurations are also provided. In a further embodiment, an electrode arrangement is comprised of first and second conductive regions of a common substrate that are separable by a division line in the substrate. For adult applications, stored energy is conducted through both conductive regions. For pediatric applications, the second region of the substrate is removed along the division line. A sensing mechanism is also provided to detect whether the electrode arrangement has been placed in an adult or pediatric configuration.

76 Claims, 6 Drawing Sheets

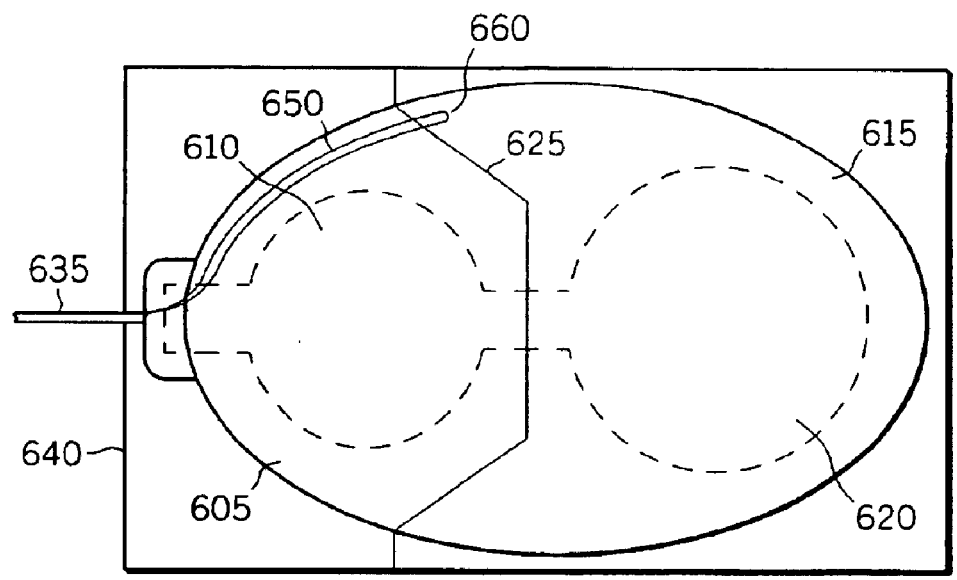
FIG. 7  600
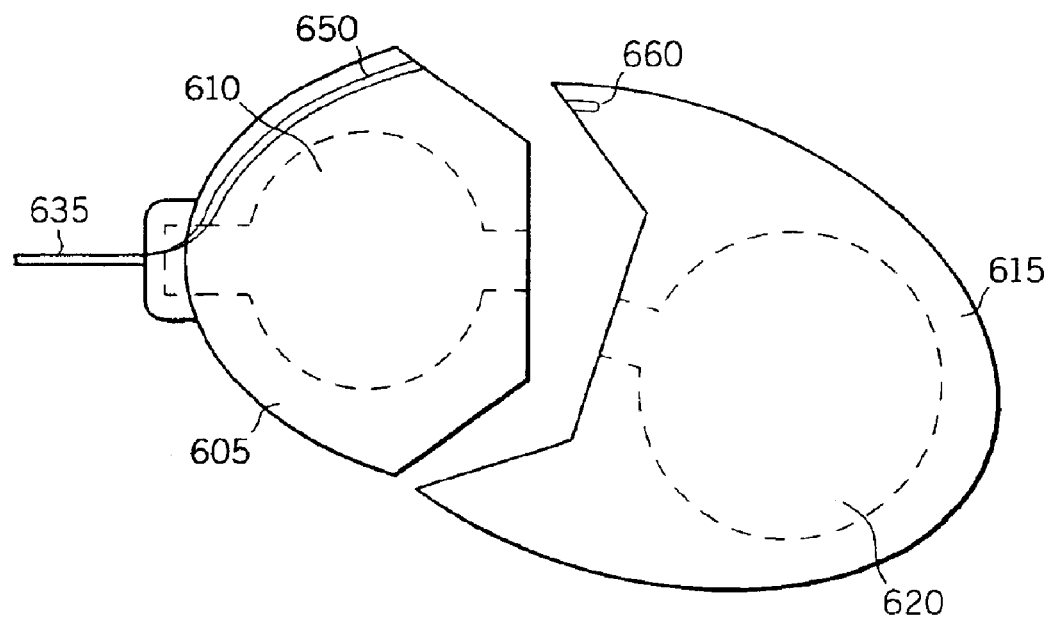
600  FIG. 8

THERAPY AND MONITORING ELECTRODES WITH PATIENT ACCOMMODATING FEATURES

FIELD OF THE INVENTION

The present invention relates generally to electrotherapy methods and apparatus. More particularly, the present invention relates to electrode configurations for electrotherapy and monitoring devices.

BACKGROUND OF THE INVENTION

Electrotherapy (e.g., defibrillation, cardioversion, and pacing) is commonly applied to patients suffering from cardiac arrest and other cardiac arrhythmias. Conventionally, electrotherapy has been applied using "hard paddles" sized appropriately for the individual undergoing treatment. Some paddle designs have integrated two or more paddle sizes utilizing clip- or slide-on/off adapters of larger or smaller size. More commonly today, "soft paddle" products are used, which provide single-use, disposable, conductive adhesive electrode pads for arrhythmia monitoring and therapy delivery. Multiple-size soft paddles or pads are offered for varying sized patients. Sizes are commonly classified for use by age or weight of the patient.

Electrotherapy devices, such as defibrillators, are becoming more widespread. This has been driven in part by the introduction and acceptance of automated external defibrillators or AEDs. AEDs are used by first responders such as police officers, firefighters, and emergency medical technicians to resuscitate victims of sudden cardiac arrest. Studies have shown that the chances of successfully resuscitating a patient decrease approximately 10 percent per minute following the onset of sudden cardiac arrest. Accordingly, for a victim of sudden cardiac arrest, time is of the essence in defibrillating the patient's heart.

AEDs are designed to be very easy to use so that rescuers without extensive medical training can provide defibrillation therapy to victims of sudden cardiac arrest. AEDs are currently carried in emergency vehicles such as police cars, paramedic vehicles, and fire trucks. AEDs are also widely deployed in areas where large numbers of people gather, such as at sports stadiums, gambling casinos, theme parks, etc. As AEDs have evolved, they have become more and more intuitive to use and are now being used by individuals with limited or no medical training. This trend is expected to continue.

AEDs almost exclusively use soft paddles for therapy delivery. At the present time, however, AEDs are also almost exclusively used on adults and are recommended only for use on patients that are 8 years old or greater. Although cardiac arrest occurs predominantly in adults, circumstances arise in which defibrillation therapy is medically indicated for children. Consequently, there is a need for defibrillator devices, especially AEDs, to have pediatric capabilities.

Soft electrode pads sized for pediatric patients are available for use with manual defibrillators. As AED designs become adapted for pediatric delivery in terms of ECG recognition and therapy dosing, the pediatric pads available today can be utilized for pediatric defibrillation and resuscitation. However, there is resistance to adding small-sized, disposable electrode pad sets to AEDs, principally due to the added cost, packaging limitations, significantly lower likelihood of use, and limited shelf-life of the electrodes. Multiple separate electrode sets with separate connectors may also be confusing to untrained users.

Some users, when faced with the need for pediatric defibrillation and resuscitation, cut down larger pads for use on children and newborns. Although a creative approach, this method can compromise the therapy delivered due to uncontrolled altering of the current distribution area of the pad, along with the potential reduction of adhesive coupling of the pad to the skin. In addition, the safety characteristics of the electrode pad are compromised by removal of some of the insulative portion of the pad that commonly surrounds the conductive area.

There is, therefore, a need for a disposable electrode pad set that can easily be adapted for use on varying sized patients at a usage cost and package size below that of multiple individual sets, with greater convenience. The present invention is directed toward satisfying this need and other shortcomings in the prior art.

SUMMARY OF THE INVENTION

The present invention is directed to multi-electrode pad arrangements that provide electrotherapy/monitoring for patients of varying size and age. In certain embodiments of the invention, the electrode arrangements include a larger electrode suitable for use in treating an adult-size patient and a smaller electrode suitable for use in treating a pediatric-size patient. The larger electrode is attached to the smaller electrode in a front-to-front, back-to-back, or front-to-back configuration. Each electrode in an electrode arrangement is adhereable to different size patients (e.g., an adult or pediatric patient) and includes a conductive surface area adapted for placement on the patient. The conductive surface areas of each electrode are protected from inadvertent adhesion and premature deterioration by a nonconductive release liner or by the physical attachment of one electrode to the other (e.g., the small electrode being releasably attached to a nonconductive backing substrate of the other electrode). Initially, the conductive surface areas of each electrode in the electrode arrangement are electrically connected to one another.

In these embodiments, if adult treatment is required, the smaller pediatric electrode may be removed from the electrode arrangement, with the larger electrode being placed on the patient. Likewise, for pediatric treatment, the larger adult electrode may be removed from the electrode arrangement, with the smaller electrode being placed on the patient. In either case, the separation of one electrode from the other preferably breaks the electrical connection between the conductive surface areas of the electrodes.

In other embodiments of the invention, an electrode arrangement is comprised of an electrically nonconductive substrate having a first region that is coplanar with a second region. Each of the first and second regions of the electrode arrangement have a conductive surface area disposed thereon. The conductive surface areas of the first and second regions are electrically connected to one another. The electrode arrangement is constructed such that the first and second regions are separable by a user of the electrode arrangement. Prior to use, a nonconductive release liner preferably protects the conductive surface areas from inadvertent adhesion and premature deterioration.

In one suitable application, when treating an adult, the release liner is discarded and the conductive surface areas of both the first and second regions of the electrode arrangement are placed on the patient. When treating a pediatric patient, the second region of the electrode arrangement is separated from the first region and discarded. The first region of the electrode arrangement is then placed on the pediatric patient. The first and second regions of the electrode arrangement may be separated along a division line that includes perforations or is otherwise weakened by crimping or scoring.

One aspect of the present invention provides a sensing mechanism for an electrotherapy or monitoring apparatus to detect which of the electrodes in the electrode arrangements are attached. Given knowledge of the electrode configuration that is used (e.g., adult or pediatric electrode configuration), the device may modify its output display in order to reflect which configuration is used. For instance, when pediatric defibrillation is required, the defibrillator may detect that the pediatric electrodes in each electrode arrangement have been placed on the patient and modify its energy output display to reflect the fact that pediatric electrodes are in use. This improved display can be achieved with or without the defibrillation device altering the energy protocol that it uses for therapy delivery.

In another aspect of the present invention, an energy attenuator is provided so that energy delivered to a patient in a pediatric configuration is less than the energy delivered in an adult configuration. In one embodiment, a resistive component is placed in series with the pediatric electrode in each electrode arrangement to dissipate a portion of the electrical energy transferred from the defibrillator. In another embodiment, an energy attenuator is provided in the form of a resistor network attached across the pediatric electrodes in the electrode arrangements to reduce the amount of electrical energy transferred through the pediatric electrodes.

Electrode arrangements constructed in accordance with the present invention thus enable caregivers to select an electrode configuration for different size patients in a manner that is less confusing and at lower cost.

DESCRIPTION OF THE DRAWINGS

The foregoing aspects and many of the attendant advantages of this invention will become more readily appreciated by reference to the following detailed description, when taken in conjunction with the accompanying drawings, wherein:

FIG. 7 is a plan view of an electrode arrangement configured according to a further embodiment of the present invention;

FIG. 8 is a plan view of the electrode arrangement shown in FIG. 6, depicting use as a pediatric defibrillator electrode, wherein an electrode section has been removed;

DETAILED DESCRIPTION OF THE PREFERRED EMBODIMENT

Figure 1:
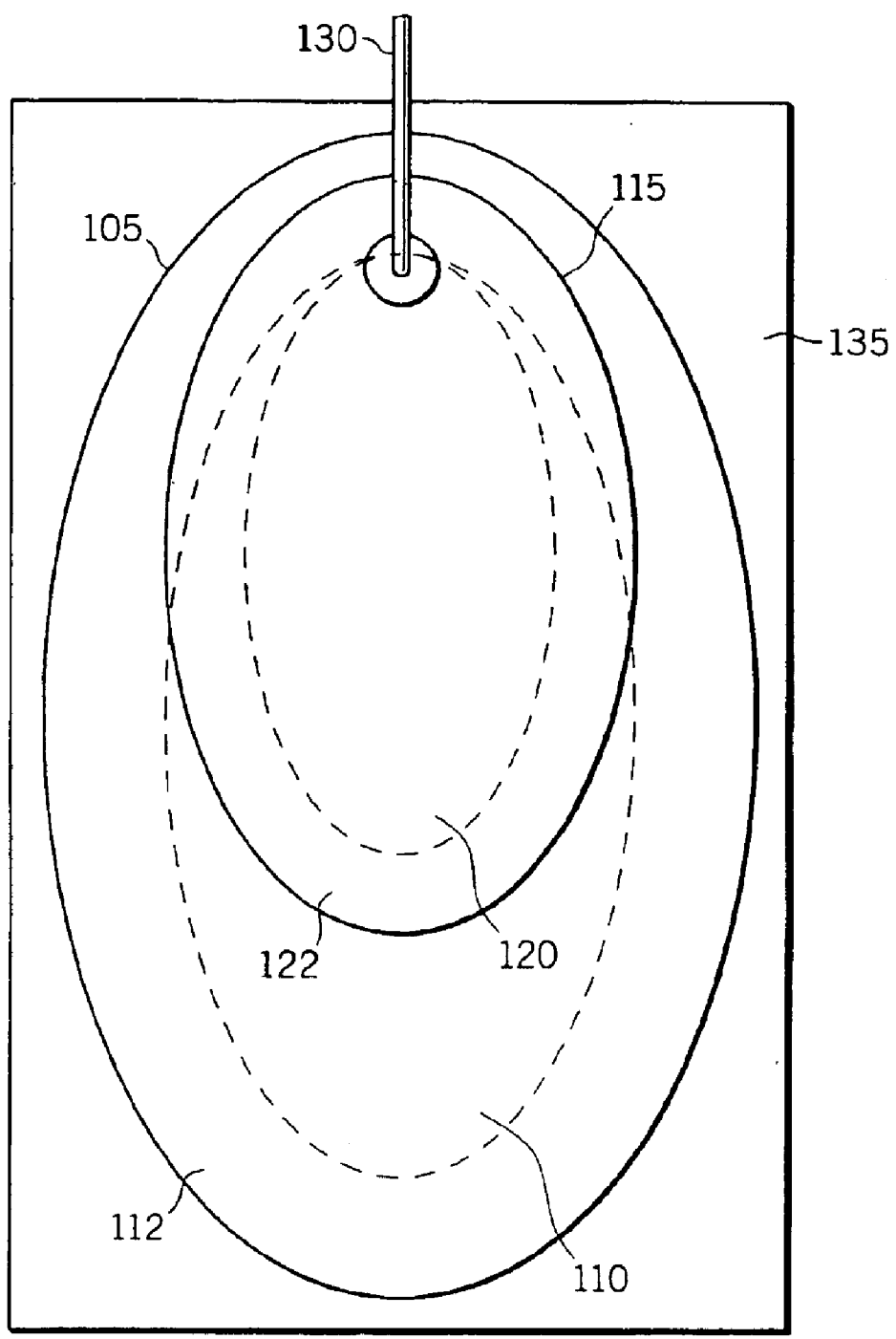
FIG. 1 is a plan view of an electrode arrangement configured according to one embodiment of the present invention.

FIG. 1 depicts an electrode arrangement 100 constructed in accordance with one embodiment of the present invention. The electrode arrangement 100 includes a smaller electrode 115, suitable for pediatric use, releasably attached to a nonconductive backing substrate of a larger electrode 105, suitable for use on an adult. Each electrode 105 and 115 has a conductive surface area 110 and 120, respectively, preferably including a conductive gel, that is used to conduct electrical energy to a patient. In this embodiment of the invention, the conductive surface area 120 is smaller than the conductive surface area 110, though that is not required.

A region of adhesive 122 surrounds some or all of the conductive surface area 120 to adhere the smaller electrode 115 to a pediatric patient. Similarly, adhesive region 112 surrounds some or all of the conductive surface area 110 to adhere the larger electrode 105 to an adult patient. A nonconductive release liner 135 is releasably attached to the bottom of the larger electrode 105 to cover the adhesive 112 and conductive surface area 110, preventing deterioration of the conductive gel and/or accidental attachment of the electrode 105 prior to use. An electrical lead wire 130 is used to couple the electrode arrangement 100 to a defibrillator or other electrotherapy device or monitor.

Electrotherapy and monitoring applications typically require two or more electrodes to be placed on the patient. For example, one electrode may be placed in an apex position and another electrode may be placed in a sternum position. In this context, the electrode arrangements described herein provide one or more electrodes for each of the apex and sternum positions. Thus, two electrode arrangements provided by the present invention would be used in this electrotherapy application. More than two electrode arrangements may be used in other applications. The particular electrode or electrodes in each electrode arrangement that are used depends on the patient and may be determined based on the age or size of the patient.

Moreover, it should be understood that the terms "adult" and "pediatric" as used herein are not meant to be limiting to any specific age group or patient size. Rather, the terms "adult" and "pediatric" are merely indications that identify general patient types for whom one or more electrodes in each electrode arrangement may be best suited. The term "infant" is also used herein in a nonlimiting manner and may b a patient type separate from or included in the "pediatrics" patient type.

In terms of FIG. 1, when performing cardiac defibrillation on an adult, the release liner 135 is removed from the bottom of the larger electrode 105, exposing both the adhesive region 112 and the conductive gel 110. The electrode 105 is applied to the skin of the adult patient, and electrical energy is conducted to the patient through the conductive gel 110 from an AED or other defibrillation device. In this case, the smaller electrode 115, along with its conductive gel 120 and adhesive 122, is simply "along for the ride" and performs no active role in the defibrillation.

When cardiac defibrillation on a pediatric patient is required, the smaller electrode 115 is peeled away from the backing substrate of the larger electrode 105 and applied to the patient. In this manner, the backing substrate of the larger electrode 105 effectively acts as a nonconductive release liner for the smaller electrode 115. The electrical lead wire 130 remains coupled to the smaller electrode 115 while the electrical coupling to the larger electrode 105 preferably tears away. The unused larger electrode 105 is discarded, and electrical energy from an AED or other defibrillation device is conducted to the patient through the conductive gel 120 of the smaller electrode 115.

Figure 2:
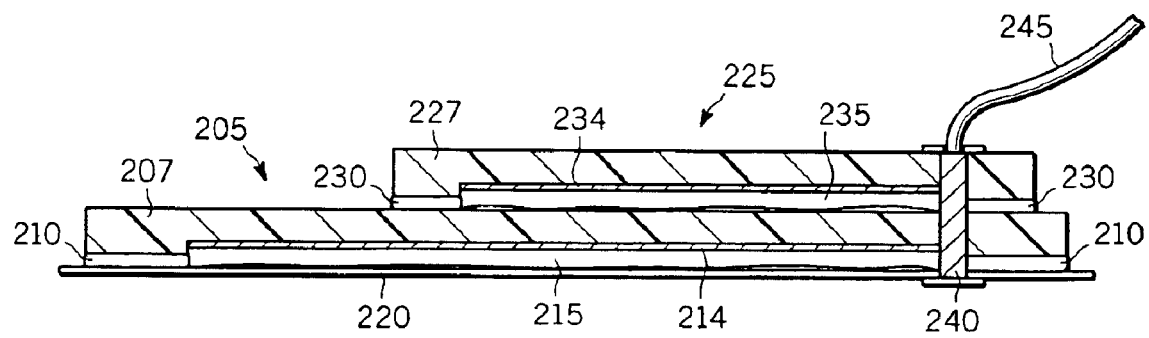
FIG. 2 is a cross-sectional transverse view of the electrode arrangement shown in FIG. 1.

FIG. 2 depicts a cross-sectional transverse view of an electrode arrangement 200 constructed as shown in FIG. 1. A smaller electrode 225, having a nonconductive backing substrate 227, is releasably attached via adhesive 230 to a nonconductive backing substrate 207 of a larger electrode 205. In turn, the larger electrode pad 205 is releasably attached via adhesive 210 to a nonconductive release liner 220. In a preferred embodiment, the nonconductive backing substrate 207 is treated with a release coating, at least in the area where the smaller electrode 225 is attached, to facilitate the release of the smaller electrode 225 from the larger electrode 205.

A plate 234 made of conductive material is preferably disposed in a central region of the smaller electrode 225. Similarly, a conductive plate 214 is preferably disposed in a central region of the larger electrode 205. Conductive gels 235 and 215 cover the conductive plates 234 and 214 respectively, and preferably cover the entire exposed area of the conductive plates 234, 214. The conductive plates 234, 214 and the conductive gels 235, 215 comprise the conductive surface areas of the smaller electrode 235 and larger electrode 205, respectfully, and distribute the electrical energy delivered to the patient. A lead wire 245, adapted to connect to an AED or other electrotherapy or monitoring device, is electrically coupled to the conductive plate 234 and the conductive plate 214 through a conductive connector 240.

As discussed above in regard to FIG. 1, when adult defibrillation is required, the nonconductive release liner 220 is peeled away from the larger electrode 205 and the larger electrode is attached to the patient. The lead wire 245 is attached to an AED or other defibrillation device. Defibrillation energy is then conducted to the patient through the lead wire 245, the conductive connector 240, the conductive plate 214, and conductive gel 215. The smaller electrode 225, while still electrically connected to the conductive connector 240, performs no active role in the defibrillation as it remains attached to the nonconductive backing substrate 207 of the larger electrode 205.

Figure 3:
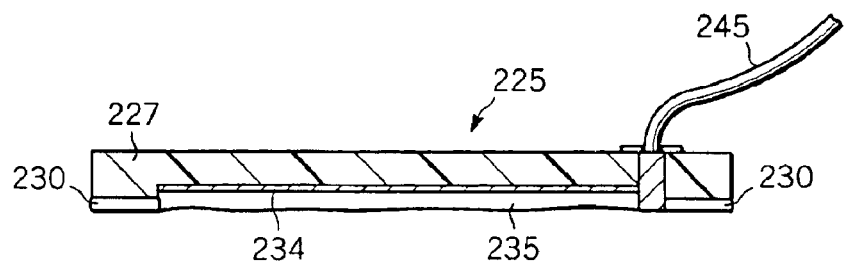
FIG. 3 is a cross-sectional transverse view of the electrode arrangement shown in FIG. 1, depicting use as a pediatric defibrillator electrode, wherein the larger adult electrode pad has been removed.

When pediatric defibrillation is required, the larger electrode 205 with release liner 220 is peeled away from the smaller electrode 225, preferably breaking the electrical coupling of connector 240 to the larger electrode 205. As shown in FIG. 3, the larger adult electrode 205 (FIG. 2) has been removed from the electrode arrangement 200 and discarded. This allows the smaller electrode 225 to be attached to a pediatric patient via adhesive 230 and gel 235. Defibrillation energy is then delivered to the patient from an AED or other defibrillation device through the lead wire 245, the conductive connector 240 that remains, the conductive plate 234, and conductive gel 235.

As is evident from the foregoing, until the larger electrode 205 is removed from the smaller electrode 225, the conductive surface areas of the respective electrodes are electrically connected via the conductive connector 240. If the larger electrode 205 is peeled away from the smaller electrode 225, the electrical connection between the electrodes is broken, as illustrated, for example, in FIG. 3. In that circumstance, only the smaller electrode 225 is placed on the patient.

Figure 4:
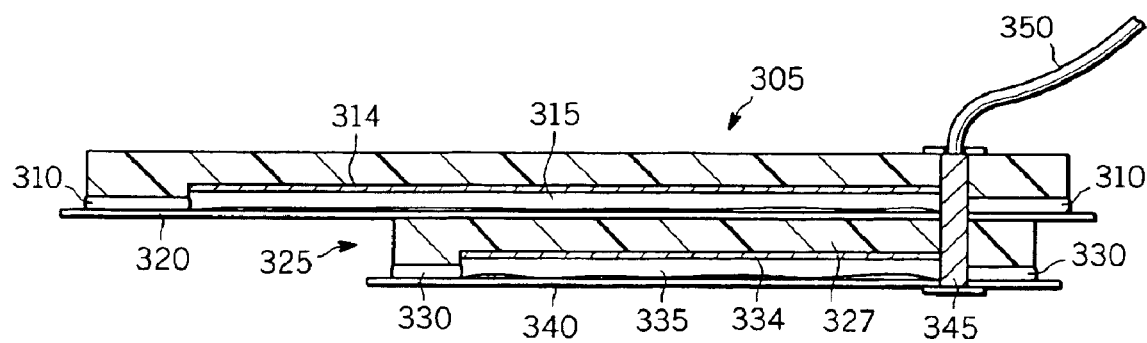
FIG. 4 is a cross-sectional transverse view of an electrode arrangement configured according to another embodiment of the present invention.

FIG. 4 illustrates an electrode arrangement 300 constructed in accordance with another embodiment of the present invention. A larger electrode 305, having a conductive plate 314 and conductive gel 315, is releasably attached via adhesive 310 to a nonconductive release liner 320 that covers the conductive gel 315. The opposite side of the nonconductive release liner 320 is attached to a nonconductive backing substrate 327 of a smaller electrode 325. The smaller electrode 325 is in turn releasably attached to a smaller nonconductive release liner 340 via adhesive 330. The nonconductive release liner 340 covers the conductive gel 335 and conductive plate 334 of the smaller electrode 325.

As with the other embodiments of the invention discussed above, when adult defibrillation is required, only the larger electrode 305 is utilized. The electrode 305 is peeled away from the nonconductive release liner 320 and smaller electrode 325, preferably breaking the electrical coupling of the smaller electrode 325 to the conductive connector 345. The nonconductive release liner 320 is discarded along with the smaller electrode 325. Defibrillation energy is delivered to the patient through the lead wire 350, conductive connector 345, conductive plate 314, and conductive gel 315.

When pediatric defibrillation is needed, however, the smaller nonconductive release liner 340 is removed, exposing adhesive 330 and conductive gel 335 for application to the patient. Defibrillation energy is delivered to the pediatric patient through the lead wire 350, conductive connector 345, conductive plate 334, and conductive gel 335. The larger electrode 305, while still connected to the nonconductive release liner 320 and smaller electrode 325, is only "along for the ride" and performs no active role in the defibrillation.

Recognizing that in some pediatric applications there may not be sufficient space on the patient for the electrodes when the larger electrode 305 remains attached to the smaller electrode 325, the electrode arrangement 300 may be configured to permit detachment of the larger electrode 305 when pediatric defibrillation is needed. In that circumstance, the electrode arrangement 300 is constructed so that the lead wire 350 remains connected to the smaller electrode 325 after the larger electrode 305 is removed. In that regard, an exemplary embodiment provides perforations in the larger electrode 305 to assist in detaching the larger electrode 305.

Figure 5:
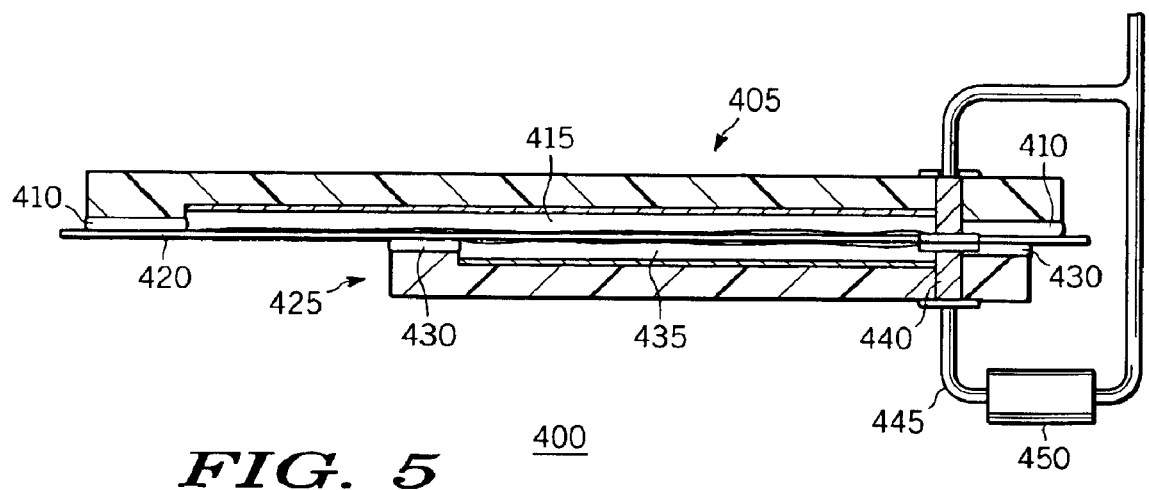
FIG. 5 is a cross-sectional transverse view of an electrode arrangement configured according to yet another embodiment of the present invention.

FIG. 5 illustrates yet another embodiment of the present invention in which electrodes in electrode arrangement 400 are arranged in a face-to-face configuration. A nonconductive release liner 420 is disposed between larger electrode 405 and smaller electrode 425, both of which are adhered to opposing sides of the release liner 420 via adhesive 410 and 430, respectively. The release liner 420 is sized to cover the face of both electrodes 405 and 425 to prevent conductive gels 415 and 435 from inadvertent attachment and premature deterioration. Lead wire 445 divides into two wires that are connected to each of the larger and smaller electrodes 405 and 425.

When adult defibrillation is required, the release liner 420 is peeled away from the larger electrode 405, and, along with smaller electrode 425, is placed away from the patient. The larger electrode 405 is then attached to the patient via adhesive 410 and gel 415. If, however, pediatric defibrillation is needed, the release liner 420 is peeled away from the smaller electrode 425, and, along with the larger electrode 405, is placed away from the patient. The smaller electrode 425 is then attached to the patient via adhesive 430 and gel 435. For either an adult or pediatric patient, defibrillation therapy is then provided by conducting electrical energy through lead wire 445, conductive connector 440, and the conductive plate and gel of the electrode 405 or 425 that is attached to the patient.

In FIG. 5, the smaller electrode 425 is also shown with an optional energy attenuator 450 that is configured to reduce the amount of electrical energy transferred to the patient through the electrode 425. The energy attenuator 450 may comprise one or more resistors that scale the energy delivered to an amount appropriate for pediatric applications. Alternatively, energy attenuation may be provided by a resistor network attached across the smaller (pediatric) electrodes in two or more electrode arrangements, as described below in more detail in reference to FIG. 12.

The electrode arrangement 400 may also be configured to use both electrodes 405 and 425 for adult defibrillation and only electrode 425 for pediatric defibrillation. In this configuration, the electrodes 405 and 425 are removed from the release liner 420 but remain electrically connected via the divided lead wire 445 which conducts electrical energy to both electrodes simultaneously. Adding the conductive area of the smaller electrode 425 to the conductive area of the larger electrode 405 may be particularly advantageous for large adult patients.

Figure 6:
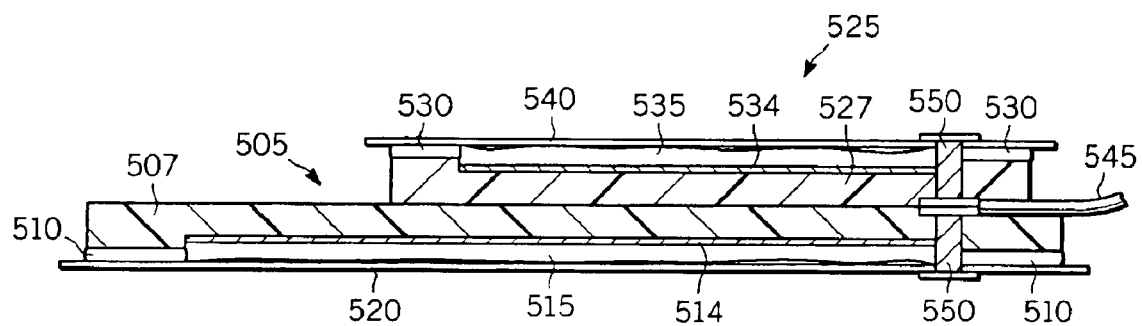
FIG. 6 is a cross-sectional transverse view of an electrode arrangement configured according to still another embodiment of the present invention.

FIG. 6 illustrates yet another embodiment of the present invention in which electrodes in electrode arrangement 500 are arranged in a back-to-back configuration. More specifically, a nonconductive backing substrate 527 of a smaller electrode 525 is attached to a nonconductive backing substrate 507 of a larger electrode 505. A nonconductive release liner 540 is attached to the smaller electrode 525, covering conductive gel 535. As for the larger electrode 505, a nonconductive release liner 520 is attached and covers conductive gel 515. A lead wire 545 is preferably coupled to the electrodes 505 and 525 between the respective backing substrates 507 and 527.

When pediatric defibrillation is contemplated, the nonconductive liner 540 is removed from the smaller electrode 525, exposing the conductive gel 535. The smaller electrode 525 is attached to the patient via adhesive 530. Defibrillation energy is then conducted through the lead wire 545, conductive connector 550, conductive plate 534, and conductive gel 535 to the patient.

When adult defibrillation is needed, however, the nonconductive liner 520 is removed, exposing the conductive gel 515. The larger electrode 505 is attached to the patient via adhesive 510. Defibrillation energy is then conducted to the patient via lead wire 545, conductive connector 550, conductive plate 514, and conductive gel 515.

In FIG. 6, the backing substrate 527 of the smaller electrode 525 may be releasably attached to the backing substrate 507 of the larger electrode 505, so that in use, the unused electrode may be removed and discarded. This configuration is advantageous in that it permits the unused electrode to be removed. For example, the larger electrode 505 may be removed in pediatric applications where there is not enough space on the pediatric patient to accommodate the larger, unused electrode 505. Alternatively, the connection between the electrode backing substrates 507 and 527 may be permanent, in which case the nonconductive release liners 520 and 540 are constructed to protect the user from unintended shocks from the unused electrode. In a further embodiment, the backing substrates 507 and 527 may be integrated to form a single nonconductive substrate with an adult (e.g., larger) conductive surface area 515 on one side and a pediatric (e.g., smaller) conductive surface area 535 on the other side.

Referring to FIGS. 7 and 8, in still another embodiment of the invention, an electrode substrate in a common plane is divided into a first electrode section 605 and a second electrode section 615 along division line 625. Division line 625 may be formed via perforation, scoring, crimping, or other method of weakening the substrate material for the purpose of guided physical separation. Conductive surface areas 610 and 620 are disposed on each of the first electrode section 605 and second electrode section 615, respectively, and are electrically coupled to each other. A lead wire 635 is electrically connected to the conductive surface area 610.

In combination, the conductive surface areas 610, 620 are sized to provide a single adult electrode, while the single conductive surface area 610, located in the first electrode section 605 proximal to the lead wire 635, is sized to provide a single pediatric electrode. An adhesive appropriate for attachment to a patient is disposed on the portion of the electrode substrate outside the conductive surface areas 610, 620. A nonconductive release liner 640 is releasably attached to the conductive surface areas 610, 620 to prevent inadvertent attachment of the electrodes and protect the conductive gel.

To provide adult defibrillation, the release liner 640 is peeled away from the electrode sections, exposing conductive surface areas 610 and 620 which are placed on the patient. Defibrillation energy from an AED or other defibrillation device is conducted through the lead wire 635 and both conductive surface areas 610, 620 to the patient. If, however, pediatric defibrillation is desired, the second electrode section 615, distal to the attachment of lead wire 635, is separated along division line 625 and discarded, thus breaking the electrical connection between the conductive surface areas 610, 620. The first electrode section 605, along with its conductive surface area 610, remains coupled to the lead wire 635 and, after removal of the release liner 640, is applied to the patient. Defibrillation therapy may then be delivered to the pediatric patient. FIG. 8 displays the discarded second electrode section 615 as removed from the first electrode section 605.

A further aspect of the present invention enables the defibrillation or monitoring device attached to the electrode arrangements to detect which electrode(s) in each electrode arrangement are being used. Referring once again to FIG. 7, one exemplary detection mechanism includes a wire 650 forming a current path in the first electrode section 605. The wire 650 is attachable to the defibrillation or monitoring device via an electrical connection in lead wire 635 that is separate from the electrical connection in lead wire 635 to the conductive surfaces areas 610, 620. A loop in the wire 650 forms a circuit closure 660, located in second electrode section 615. An alternative circuit closure 660 includes a separate conducting plate in the second electrode section 615, which electrically connects the ends of the wire 650 when the second electrode section 615 is connected to the first electrode section 605.

When using the electrode arrangement 600 for adult defibrillation, both sections 605, 615 remain connected as described above, and circuit closure 660 provides a short-circuit termination to the wire 650. When using the electrode arrangement 600 for pediatric defibrillation, as shown in FIG. 8, the connection with wire 650 is broken and circuit closure 660 is removed and discarded along with second electrode section 615. The wire 650 therefore terminates in an open circuit. This difference in terminating impedance allows an external defibrillation or monitoring device to detect the configuration of the electrode arrangement 600 that is being used: a closed circuit, or zero impedance, in the wire 650 indicates an adult configuration while an open circuit, or high impedance, in the wire 650 indicates a pediatric configuration.

Figure 9:
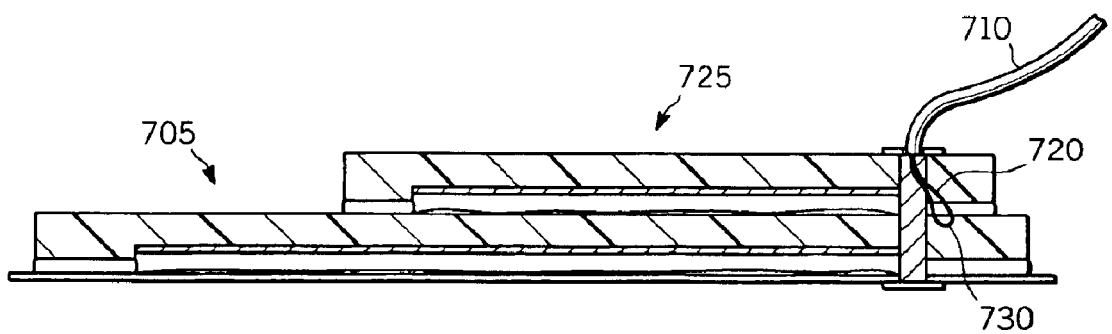
FIG. 9 is a cross-sectional transverse view of the electrode arrangement shown in FIGS. 1 and 2, and includes a sensing mechanism for detecting the configuration in use.

Referring to FIG. 9, an electrode arrangement 700 as shown in FIGS. 1 and 2 provides a similar exemplary sensing mechanism that includes a wire 720 forming a current path attached to a separate electrical connection within lead wire 710. The wire 720 extends through smaller electrode 725 to connect with circuit closure 730, in larger electrode 705. When using the electrode arrangement 700 for adult defibrillation, the circuit closure 730 provides a short-circuit termination for the wire 720. When pediatric defibrillation occurs, however, the connection with wire 720 is broken and the larger electrode 705 is removed and discarded along with the circuit closure 730. The wire 720 therefore terminates in an open circuit, detectable by the defibrillation or monitoring device, indicating a pediatric configuration for the electrode arrangement 700.

Figure 10:
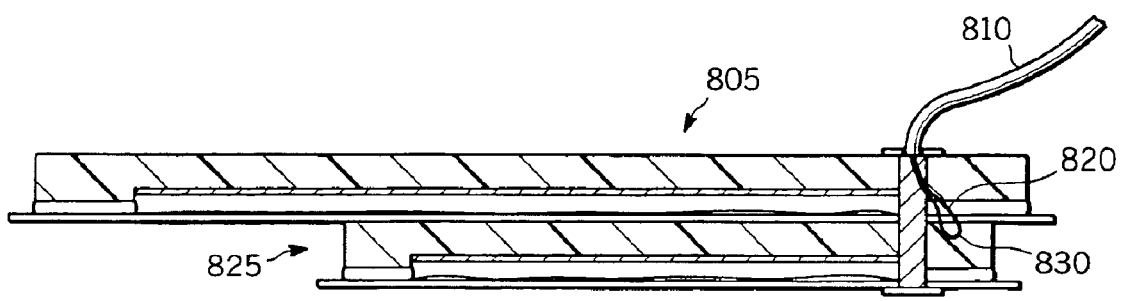
FIG. 10 is a cross-sectional transverse view of the electrode arrangement shown in FIG. 4 including a sensing mechanism for detecting the configuration in use.

In another electrode arrangement 800, shown in FIG. 10, larger electrode 805 is positioned on the back of smaller electrode 825, such as shown and described in FIG. 4. A sensing mechanism includes a wire 820 forming a current path attached to a separate electrical connection within lead wire 810. The wire 820 extends through the larger electrode 805 to connect with circuit closure 830, which may be a loop in the wire 820, in the smaller electrode 825. When using the electrode arrangement 800 for pediatric defibrillation, the circuit closure 830 provides a short-circuit termination for the wire 820. When adult defibrillation occurs, however, the connection with wire 820 is broken and the smaller electrode 825 is removed and discarded along with the circuit closure 830. The wire 820 therefore terminates in an open circuit, again detectable by the defibrillation or monitoring device, indicating an adult configuration for the electrode arrangement 800.

A sensing mechanism as described above may also be incorporated into the electrode arrangements shown in FIGS. 5 and 6. In FIG. 5, a sensing wire as described above (not illustrated) may extend through the smaller electrode 425 and connect with a circuit closure in the nonconductive liner 420. When adult defibrillation is performed, the larger electrode 405 is used and the liner 420 remains attached to the smaller electrode 425, maintaining a closed circuit in the sensing wire. When pediatric defibrillation is performed, the liner 420 is removed from the smaller electrode 425, breaking the connection with the sensing wire and resulting in an open circuit that is detectable by the defibrillation or monitoring device to indicate a pediatric electrode configuration.

Similarly, with the electrode arrangement 500 shown in FIG. 6, a sensing wire as described above may extend through the smaller electrode 525 and connect with a circuit closure in the nonconductive liner 540. Removal of the liner 540 for a pediatric application results in an open circuit in the sensing wire. For an adult application, the nonconductive liner 520 is removed while liner 540 remains attached, keeping a closed circuit in the sensing wire. Alternatively, the sensing wire may be incorporated into the larger electrode 505, with an open circuit (from removing the liner 520) indicating an adult electrode configuration, and a closed circuit (from keeping the liner 520 attached) indicating a pediatric electrode configuration.

In all of the above embodiments, the sensing wire may be a physical strand of conductive material incorporated into the electrode arrangement. Alternatively, the wire may be formed from an etched or printed circuit line incorporated into the electrodes. Other sensing mechanisms for use in the present invention may include active electronics that determine and report which electrode is being used, or other passive mechanisms (e.g. measuring a change in inductance or capacitance from removal of one of the electrodes or nonconductive liners from the electrode arrangement).

Figure 11:
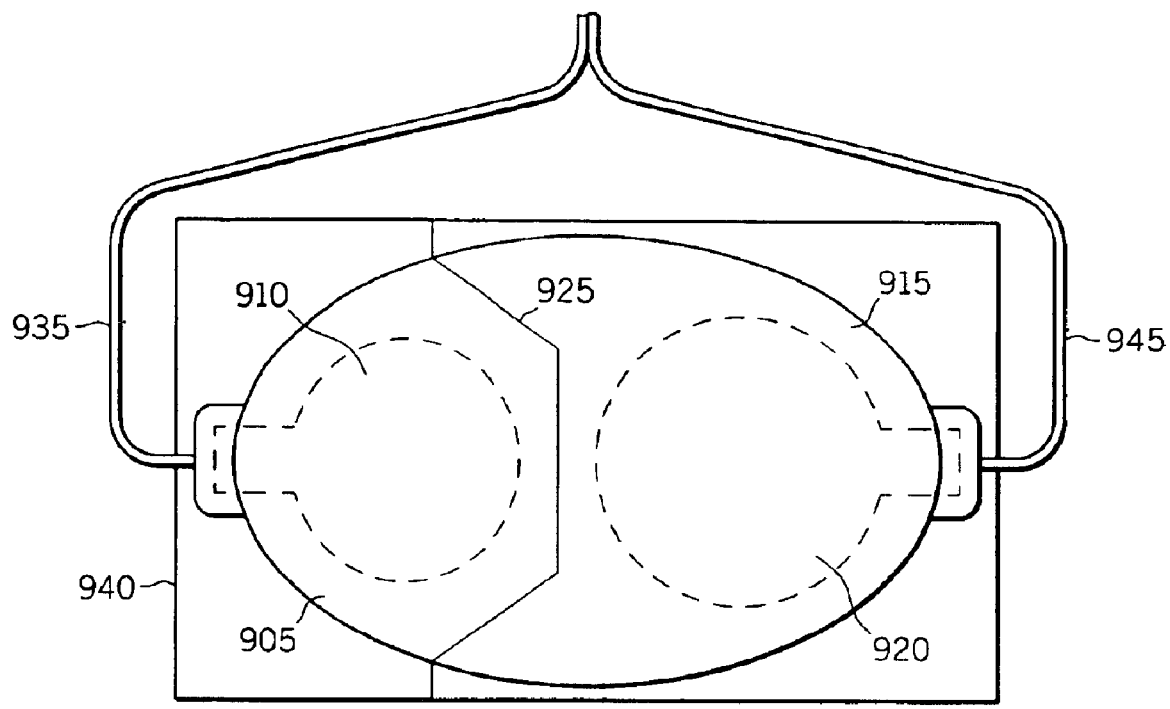
FIG. 11 is a plan view of an electrode arrangement configured according to yet a further embodiment of the present invention.

FIG. 11 illustrates yet another embodiment similar in form to the embodiment shown in FIG. 7. In FIG. 11, electrode arrangement 900 includes a first electrode 905 that is coplanar with and connected to second electrode 915. The first and second electrodes 905, 915 are separable along division line 925.

Conductive lead wire 935 is electrically connected to conductive surface area 910 that is centrally disposed on the first electrode 905. Similarly, lead wire 945 is electrically connected to conductive surface area 920 of the second electrode 915. The lead wires 935 and 945 are adapted to connect to an AED or other defibrillator or monitoring device. Initially, the lead wires 935, 945 may be electrically connected to one another, either in the device to which they are connected, or in a component (e.g., a switch) connected to the lead wires. As discussed below, depending on which electrodes are used, the lead wires 935, 945 may be electrically separated from one another (if initially connected), with electrical energy being conducted to only one of the electrodes 905, 915.

In one suitable application, the conductive surface areas 910, 920 combined are sized to provide a single adult electrode, while the conductive surface areas 910 or 920 alone are each sized to provide a single pediatric electrode. Since, as illustrated, the conductive surface area 920 is larger than the conductive surface area 910, the second electrode 915 may be selected for larger pediatric patients and the first electrode 905 may be selected for smaller pediatric (e.g., infant) patients.

Further, an adhesive suitable for attachment to a patient is disposed on a portion of the electrode substrate outside the conductive surface areas 910, 920. A nonconductive release liner 940 is releasably attached to the conductive surface areas 910, 920 to prevent inadvertent attachment of the electrodes and to protect the conductive gel.

Adult defibrillation is provided by peeling away the release liner 940 from the electrodes, thus exposing the conductive surface areas 910, 920 which are placed on the patient. Defibrillation energy from an AED or other defibrillation device is then conducted through the lead wires 935, 945 to both conductive surface areas 910, 920 on the patient.

When pediatric defibrillation is desired, the first electrode 905 and the second electrode 915 are preferably separated from one another. The release liner 940 is removed from the electrode 905 or 915 selected for placement on the patient.

The defibrillation device to which the electrode arrangement 900 is connected is preferably configured to detect whether one or both of the electrodes 905, 915 have been placed on a patient. In that regard, the defibrillation device may communicate an impedance-sensing signal through the conductive surface areas 910, 920 of the two electrodes to determine whether one or both of the electrodes have been placed on a patient. Leads on/off circuitry that is present in conventional defibrillators may also be used to determine which electrodes have been applied to the patient.

When it is determined that only one of the electrodes 905 or 915 has been applied to a patient, the unapplied electrode may be electrically isolated from the applied electrode. In that regard, the defibrillation device detecting whether one or both of the electrodes have been applied to the patient may isolate the lead wire 935 or 945 that connects to the unapplied electrode.

With knowledge of which electrode has been placed on the patient, the defibrillation or monitoring device may modify its display in order to reflect the fact that pediatric or adult electrodes are in use. For a defibrillator, this improved monitoring or status display may be achieved without the defibrillation device altering the energy protocol delivered to the electrode arrangements. Energy attenuation may be provided in the pediatric electrode to scale the energy output from a therapy device for pediatric applications. See, e.g., the energy attenuator 450 in FIG. 5. Each state of a given electrode arrangement possesses an identifiable electrical impedance such that a compatible defibrillation device may distinguish between adult or pediatric electrodes being used for defibrillation.

The embodiments of the invention described herein are appropriate for electrode arrangements for both adult/pediatric or pediatric/neonatal configurations. For a pediatric/neonatal configuration, the larger electrode would be configured for a pediatric patient while the smaller electrode would be configured for a neonatal patient. Although the frequency of need for neonatal defibrillation electrodes is typically small, a pediatric/neonatal embodiment would be advantageous, for example, in a pediatric ward of a hospital.

Furthermore, electrode arrangements may be constructed in accordance with the present invention such that the electrodes in each arrangement are of substantially identical size, but attenuate the energy delivered from an AED or other defibrillation device differently. In this manner, one electrode in the electrode arrangement would deliver energy appropriate for pediatric defibrillation, while the other electrode in the electrode arrangement would deliver energy suitable for adult defibrillation. The electrode for pediatric defibrillation would normally transfer less energy to the patient than the electrode for adult defibrillation.

Figure 12:
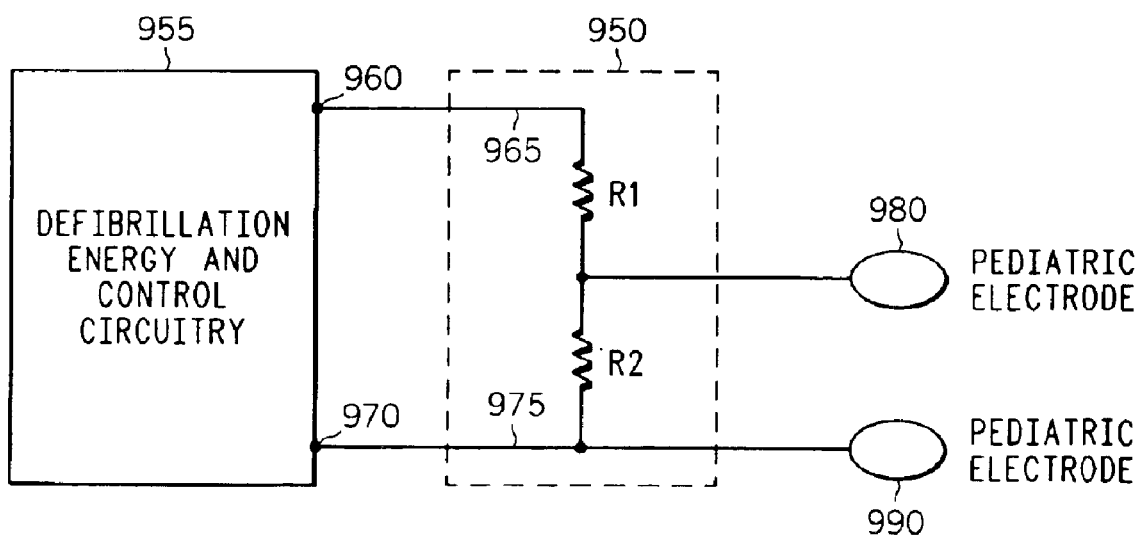
FIG. 12 is a schematic diagram of an energy attenuator for use in accordance with the present invention.

The energy attenuation in this aspect of the invention may be provided by a resistor network, as shown in FIG. 12. Energy attenuation may be provided by an energy attenuation circuit 950 that is used to dissipate a portion of the energy delivered from the defibrillation energy and control circuitry 955 so that a low energy pulse is delivered to a pediatric patient. In the particular embodiment shown in FIG. 12, two resistors R1 and R2 are connected to form an energy divider, with the pediatric electrode of each of the electrode arrangements to be placed on the patient being connected across one of the resistors. In FIG. 12, resistor R1 is coupled to an output port 960 of the defibrillation energy and control circuitry 955 by a coupler 965, while resistor R2 is coupled to an output port 970 by a coupler 975. The energy attenuation circuit 950 is coupled to pediatric electrodes 980 and 990 of two electrode arrangements provided by the present invention. The first pediatric electrode 980 is coupled to a circuit node between the resistors R1 and R2. The second pediatric electrode 990 is coupled to the other end of the resistor R2, which is connected to the output port 970. Suitable values for the resistors R1 and R2 range from 5 to 100 ohms in this embodiment of the invention. Other resistor values may be chosen for other embodiments of the invention.

As illustrated in FIG. 12, the resistors R1 and R2 are in series in a circuit path between the output ports 960 and 970, and the resistor R2 is in parallel with a patient (not shown) connected across the pediatric electrodes 980, 990. When the impedance of resistor R1 is significantly greater than the impedance of the patient, the resistor R1 will absorb most of the defibrillation pulse energy. The resistor R2, being in parallel with the patient, will absorb a portion of the energy in accordance with the current that flows through it rather than through the patient. The voltage drop across the resistor R2 and the patient will be approximately the same.

The resistance ratio of the two resistors R1 and R2 is preferably predetermined so that a predetermined percentage of the defibrillation energy from the defibrillation energy and control circuitry 955 is provided to the patient. The resistance values are determined according to a predetermined ratio so that in conjunction with the patient impedance, the energy delivered to the patient is scaled to a desired energy level. For example, the energy attenuation circuit 950 may have a 10:1 energy reduction ratio. Accordingly, energy delivered from the defibrillation circuitry 955 ranging from 2 joules to 360 joules would be reduced to energy ranging from 0.2 joules to 36 joules. An isolation network (not shown) may also be connected to the energy attenuation circuit 950 to permit ECG signals to be more accurately monitored via the pediatric electrodes placed on the patient. Suitable energy attenuation circuits as described above are further described in copending application Ser. No. 09/684,506 titled ENERGY ADJUSTING CIRCUIT FOR PRODUCING AN ULTRA-LOW ENERGY DEFIBRILLATION WAVEFORM WITH FIXED PULSE WIDTH AND FIXED TILT, assigned to the assignee of the present invention, and incorporated by reference herein. Other energy adjusting circuits as described above are known in the art. See, e.g., U.S. Pat. Nos. 5,674,253 and 6,134,468, the disclosures of which are also incorporated by reference herein.

While several embodiments of the invention have been illustrated and described, it will be appreciated that various changes can be made therein without departing from the spirit and scope of the invention. For example, other alternative embodiments may include three or more electrodes or electrode regions that are electrically connected to each other until the time of use when one or more of the electrodes is selected and the other electrodes or electrode regions are removed. Accordingly, the scope of the invention should not be determined from the specific embodiments described herein but in reference to the following claims and equivalents thereto.

What is claimed is:

1. An electrode arrangement, comprising:
   a first electrode disposed in a first plane and a second electrode disposed in a second plane that is other than the first plane, at least a portion of the first electrode overlying at least a portion of the second electrode, each of the first and second electrodes having a back formed of an electrically nonconductive substrate and a face that includes a conductive surface area adapted for placement on a patient, the face of the first electrode is releasably attached to a first nonconductive liner, and the face of the second electrode is releasably attached to a second nonconductive liner, and the backs of the first and second electrodes are attached to each other;
   wherein the conductive surface area of the second electrode is smaller than the conductive surface area of the first electrode;
   wherein the conductive surface areas of the first and second electrodes are electrically connected to each other; and wherein if the electrical connection between the conductive surface areas of the first and second electrodes is broken, the conductive surface area of only one of the first or second electrodes is placed on the patient.

2. The electrode arrangement of claim 1, wherein the backs of the first and second electrodes are integrated to form a single nonconductive substrate.

3. The electrode arrangement of claim 1, further comprising a sensing mechanism that senses whether the conductive surface area of the first or second electrode is to be placed on the patient.

4. An electrode arrangement, comprising:
a first electrode disposed in a first plane and a second electrode disposed in a second plane that is other than the first plane, at least a portion of the first electrode overlying at least a portion of the second electrode, each of the first and second electrodes having a back formed of an electrically nonconductive substrate and a face that includes a conductive surface area adapted for placement on a patient, the face of the first electrode is releasably attached to a first nonconductive liner, and the face of the second electrode is releasably attached to a second nonconductive liner, and the backs of the first and second electrodes are attached to each other;
wherein the conductive surface areas of the first and second electrodes are electrically connected to each other;
wherein if the electrical connection between the conductive surface areas of the first and second electrodes is broken, only one of the first or second electrodes is placed on the patient; and
wherein the second electrode is configured to transfer less electrical energy to the patient than the first electrode when electrical energy is to be delivered to the patient.

5. The electrode arrangement of claim 4, wherein the backs of the first and second electrodes are integrated to form a single nonconductive substrate.

6. The electrode arrangement of claim 4, further comprising a sensing mechanism that senses whether the conductive surface area of the first or second electrode is to be placed on the patient.

7. The electrode arrangement of claim 4, further comprising an energy attenuator that causes the second electrode to transfer less electrical energy to the patient than the first electrode.

8. The electrode arrangement of claim 4, wherein the conductive surface area of the second electrode is smaller than the conductive surface area of the first electrode.

9. An electrode arrangement, comprising:
an electrically nonconductive substrate having a first region coplanar with a second region;
a first electrode having a first electrically conductive area disposed on the first region, the first electrically conductive area having a first outside boundary surface;
a second electrode having a second electrically conductive area disposed on the second region, the second electrically conductive area having a second outside boundary surface;
a sensing mechanism that senses which of the first and second regions has been placed on a patient;
wherein the sensing mechanism causes a change in operation of energy delivery to the patient if only one of the first or second regions has been placed on the patient;
wherein only a first portion of the first outside boundary surface of the first electrically conductive area is physically coupled to only a second portion of the second outside boundary surface of the second electrically conductive area so that the first electrically conductive area is in electrical communication with the second electrically conductive area;
wherein the first portion is less than the entire first outside boundary surface of the first electrically conductive area and the second portion is less than the entire second outside boundary surface of the second electrically conductive area;
wherein the first and the second electrodes are configured to serve as a single electrode when connected together; and
wherein the first and second regions are separable by a user of the electrode arrangement so that one of the first and the second electrodes may be used independent of the other.

10. The electrode arrangement of claim 9, wherein the sensing mechanism that senses whether the second region has been separated from the first region.

11. The electrode arrangement of claim 10, further comprising an energy attenuator that causes less electrical energy to be transferred through the first conductive surface area of the first region if the second region has been separated from the first region.

12. The electrode arrangement of claim 9, wherein the first and second regions are separable by one or more perforations in the substrate.

13. The electrode arrangement of claim 9, wherein the first and second regions are separable along a weakened division in the substrate, the weakened division created by crimping a portion of the substrate.

14. The electrode arrangement of claim 9, wherein the first and second regions are separable along a weakened division in the substrate, the weakened division created by scoring a portion of the substrate.

15. A method of placing electrodes on a patient, comprising:
providing a plurality of electrode arrangements, each electrode arrangement comprising a first electrode disposed in a first plane and a second electrode disposed in a second plane that is other than the first plane, at least a portion of the first electrode overlying at least a portion of the second electrode, each of the first and second electrodes having a back formed of an electrically nonconductive substrate and a face that includes a conductive surface area that is adapted for placement on a patient, a nonconductive liner having opposing sides, wherein the face of the first electrode is releasably attached to one side of the liner and the face of the second electrode is releasably attached to the opposing side of the liner and wherein the conductive surface areas of the first and second electrodes are electrically connected to each other;
separating the first and second electrodes;
for each electrode arrangement, placing the conductive surface area of the second electrode on the patient if the patient is an adult patient; and
for each electrode arrangement, placing the conductive surface area of only the first electrode on the patient if the patient is a pediatric patient.

16. The method of claim 15, wherein for each electrode arrangement, the conductive surface area of the first electrode is smaller than the conductive surface area of the second electrode.

17. The method of claim 15, further comprising electrically disconnecting the second electrode from the first electrode in each electrode arrangement if the patient is a pediatric patient.

18. The method of claim 15, further comprising providing a sensing mechanism that senses whether only the conductive surface area of the first electrode is to be placed on the patient.

19. The method of claim 15, further comprising connecting the plurality of electrode arrangements to an electrotherapy device and transferring electrical energy from the electrotherapy device to the patient through the electrodes placed on the patient.

20. The method of claim 19, further comprising transferring less electrical energy to the patient through the first electrode if the patient is a pediatric patient.

21. A medical device, comprising:
  (a) a plurality of electrode arrangements adapted for placement on a patient, each electrode arrangement comprising a first electrode disposed in a first plane and a second electrode disposed in a second plane other than the first plane, at least a portion of the first electrode overlying at least a portion of the second electrode, each of the first and second electrodes having a back formed of an electrically nonconductive substrate and a face that includes a conductive surface area adapted for placement on a patient, the face of the first electrode is releasably attached to a first nonconductive liner, and the face of the second electrode is releasably attached to a second nonconductive liner, and the backs of the first and second electrodes are attached to each other, wherein the conductive surface areas of the first and second electrodes are electrically connected to one other, and wherein for each electrode arrangement, if the electrical connection between the conductive surface areas is broken, the conductive surface area of only one of the first or second electrodes in the electrode arrangement is placed on the patient; and
  (b) circuitry in communication with the plurality of electrode arrangements, said circuitry being configured to transfer electrical energy to or receive electrical energy from the patient after at least one electrode in each of the electrode arrangements has been placed on the patient.

22. The medical device of claim 21, further comprising a sensing mechanism that senses which electrode in each electrode arrangement has been placed on the patient.

23. The medical device of claim 22, wherein the medical device is further configured to modify the electrical energy to be transferred to the patient based on which electrodes in the plurality of electrode arrangements have been placed on the patient.

24. The medical device of claim 22, wherein the medical device is further configured to modify a display of information to a user of the medical device based on which electrodes in the plurality of electrode arrangements have been placed on the patient.

25. The medical device of claim 22, wherein the medical device is further configured to modify the waveform of the electrical energy to be transferred to the patient based on which electrodes in the plurality of electrode arrangements have been placed on the patient.

26. The medical device of claim 22, wherein the medical device is further configured to modify the routing of electrical energy to the electrodes in the plurality of electrode arrangements based on which electrodes in the plurality of electrode arrangements have been placed on the patient.

27. The medical device of claim 21, wherein the first and second electrodes in each electrode arrangement are separable prior to placement on the patient.

28. The medical device of claim 27, wherein for each electrode arrangement, the medical device is further configured to electrically disconnect the second electrode from the first electrode if the first and second electrodes in the electrode arrangement are separated.

29. The medical device of claim 21, wherein for each electrode arrangement, the conductive surface area of the first electrode is smaller than the conductive surface area of the second electrode.

30. An electrode arrangement comprising:
  an electrically nonconductive substrate having a first region and a second region other than the first region, the first region coplanar with and exclusive of the second region;
  a first electrode disposed entirely on the first region, the first electrode having a conductive region;
  a second electrode disposed entirely on the second region, the second electrode having a conductive region smaller than the conductive region of the first electrode; and
  a sensing mechanism that senses which of the first and second regions has been placed on a patient;
  wherein the sensing mechanism causes a change in operation of energy delivery to the patient if only one of the first or second regions has been placed on the patient;
  wherein the first electrode and the second electrode are electrically connected to one another and are configured to serve as a single electrode when connected to one another; and
  wherein the first and second regions are separable by a user of the electrode arrangement so that one of the first and the second electrodes may be used independently of the other.

31. The electrode arrangement of claim 30, wherein the sensing mechanism senses whether the second region has been separated from the first region.

32. The electrode arrangement of claim 31, further comprising an energy attenuator that causes less electrical energy to be transferred through the first electrode if the second electrode has been separated from the first electrode.

33. The electrode arrangement of claim 30, wherein the first and second regions are separable by one or more perforations in the substrate.

34. The electrode arrangement of claim 30, wherein the first and second regions are separable along a weakened division in the substrate, the weakened division created by crimping a portion of the substrate.

35. The electrode arrangement of claim 30, wherein the first and second regions are separable along a weakened division in the substrate, the weakened division created by scoring a portion of the substrate.

36. A method of placing electrodes on a patient, the method comprising:
  providing a plurality of electrode arrangements, each electrode arrangement comprising an electrically nonconductive substrate having a first region coplanar with a second region, wherein upon each region is disposed a conductive surface area having an outside boundary surface, wherein only a portion of each of the outside boundary surfaces are coupled so that the conductive surface areas are in electrical communication with one another and wherein the portion of each of the outside boundary surfaces is less than the entire respective outside boundary surface;
  for each electrode arrangement, placing the conductive surface area of or the combined first and second regions on the patient if the patient is of a first size; and for each electrode arrangement, placing the conductive surface area of the first region on the patient if the patient is of a second size and for each electrode arrangement, placing the conductive surface area of the second region on the patient if the patient is of a third size.

37. The method of claim 36, wherein for each electrode arrangement, the conductive surface area of the first region is smaller than the conductive surface area of the second region.

38. The method of claim 36, further comprising electrically disconnecting the conductive surface area of the second region from the conductive surface area of the first region in each electrode arrangement if the patient is a pediatric patient.

39. The method of claim 36, further comprising providing a sensing mechanism that senses whether only the conductive surface area of the first region is to be placed on the patient.

40. The method of claim 36, further comprising connecting the plurality of electrode arrangements to an electrotherapy device and transferring electrical energy from the electrotherapy device to the patient through the conductive surface areas placed on the patient.

41. The method of claim 36, further comprising placing the conductive surface area of the first region on the patient and transferring less electrical energy to the patient through the conductive surface area of the first region if the patient is a pediatric patient.

42. A method of placing electrodes on a patient, the method comprising:
    providing a plurality of electrode arrangements, each electrode arrangement having an electrically nonconductive substrate having a first region coplanar with a second region that is exclusive of the first region, a first electrode having a conductive area disposed entirely on the first region and a second electrode having a conductive area disposed entirely on the second region, wherein the first electrode and the second electrode are electrically connected to one another but the conductive areas of the first electrode and the second electrode are not physically connected to one another;
    for each electrode arrangement, placing the combined first and second electrode on the patient if the patient is a first size; and
    for each electrode arrangement, separating the first and second regions and placing the first electrode on the patient if the patient is a second size and for each electrode arrangement, separating the first and second regions and placing the second electrode on the patient if the patient is a third size.

43. The method of claim 42, wherein for each electrode arrangement, a conductive surface area of the first electrode is smaller than a conductive surface area of the second electrode.

44. The method of claim 42, further comprising electrically disconnecting the second electrode from the first electrode in each electrode arrangement if the patient is a pediatric patient.

45. The method of claim 42, further comprising providing a sensing mechanism that senses whether only the first electrode is to be placed on the patient.

46. The method of claim 42, further comprising connecting the plurality of electrode arrangements to an electrotherapy device and transferring electrical energy from the electrotherapy device to the patient through the electrodes placed on the patient.

47. The method of claim 42, further comprising placing the first electrode on the patient and transferring less electrical energy to the patient through the first electrode if the patient is a pediatric patient.

48. A medical device comprising:
    a plurality of electrode arrangements adapted for placement on a patient, each electrode arrangement comprising an electrically nonconductive substrate having a first region coplanar with a second region, wherein upon each region is disposed an electrode comprising an electrically conductive surface area having an outside boundary surface, and wherein:
        only a portion of each of the outside boundary surfaces are coupled so that the conductive surface areas are in electrical communication with one another;
        the portion of each of the outside boundary surfaces is less than the entire respective outside boundary surfaces; and
        if the electrical communication between the conductive surface areas is broken, the conductive surface area the first region in the electrode arrangement is placed on the patient if the patient is of a first size and the conductive surface area of the second region in the electrode arrangement is placed on the patient if the patient is of a second size; and
    circuitry in communication with the plurality of electrode arrangements, the circuitry being configured to transfer electrical energy to or receive electrical energy from the patient after at least one of the conductive surfaces has been placed on the patient.

49. The medical device of claim 48, further comprising a sensing mechanism that senses which conductive surface areas in each electrode arrangement has been placed on the patient.

50. The medial device of claim 49, wherein the medical device is further configured to modify the electrical energy to be transferred to the patient based on which conductive surface areas in the plurality of electrode arrangements have been placed on the patient.

51. The medical device of claim 49, wherein the medical device is further configured to modify a display of information to a user of the medical device based on which conductive surface areas in the plurality of electrode arrangements have been placed on the patient.

52. The medical device of claim 49, wherein the medical device is further configured to modify the waveform of the electrical energy to be transferred to the patient based on which conductive surface areas in the plurality of electrode arrangements have been placed on the patient.

53. The medical device of claim 49, wherein the medical device is further configured to modify the routing of electrical energy to the conductive surface areas in the plurality of electrode arrangements based on which conductive surface areas in the plurality of electrode arrangements has bean placed on the patient.

54. The medical device of claim 48, wherein for each electrode arrangement, the conductive surface area of the first region is smaller than the conductive surface area of the second electrode.

55. A medical device comprising:
    a plurality of electrode arrangements adapted for placement on a patient, each electrode arrangement comprising an electrically nonconductive substrate having a first region coplanar with a second region that is exclusive of the first region, a first electrode having a conductive area disposed entirely on the first region and a second electrode having a conductive area disposed entirely on the second region, wherein the first electrode and the second electrode are electrically connected to one another but the conductive areas of the first electrode and the second electrode are not physically connected to one another, and wherein, for each electrode arrangement, if the electrical connection between the first and second electrodes is broken, only the first electrode in the electrode arrangement is placed on the patient; and circuitry in communication with the plurality of electrode arrangements, the circuitry being configured to transfer electrical energy to or receive electrical energy from the patient after at least one of the conductive surfaces has been placed on the patient if the patient is of a first size and only the second electrode in the electrode arrangement is placed on the patient if the patient is of a second size.

56. The medical device of claim 55, further comprising a sensing mechanism that senses which electrodes in each electrode arrangement have been placed on the patient.

57. The medial device of claim 56, wherein the medical device is further configured to modify the electrical energy to be transferred to the patient based on which electrodes in the plurality of electrode arrangements have been placed on the patient.

58. The medical device of claim 56, wherein the medical device is further configured to modify a display of information to a user of the medical device based on which electrodes in the plurality of electrode arrangements have been placed on the patient.

59. The medical device of claim 56, wherein the medical device is further configured to modify the waveform of the electrical energy to be transferred to the patient based on which electrodes in the plurality of electrode arrangements have been placed on the patient.

60. The medical device of claim 56, wherein the medical device is further configured to modify the routing of electrical energy to the electrodes in the plurality of electrode arrangements based on which electrodes in the plurality of electrode arrangements have been placed on the patient.

61. The medical device of claim 56, wherein for each electrode arrangement, a conductive surface area of the first electrode is smaller than a conductive surface area of the second electrode.

62. An electrode arrangement, comprising:

a first electrode disposed in a first plane and a second electrode disposed in a second plane that is other than the first plane, at least a portion of the first electrode overlying at least a portion of the second electrode, each of the first and second electrodes having a back formed of an electrically nonconductive substrate and a face that includes a conductive surface area adapted for placement on a patient, a nonconductive liner having opposing sides;

wherein the face of the first electrode is releasably attached to one side of the liner and the face of the second electrode is releasably attached to the opposing side of the liner;

wherein the conductive surface areas of the first and second electrodes are electrically connected to each other;

wherein if the electrical connection between the conductive surface areas of the first and second electrodes is broken, only one of the first or second electrodes is placed on the patient; and wherein the second electrode is configured to transfer less electrical energy to the patient than the first electrode when electrical energy is to be delivered to the patient.

63. The electrode arrangement of claim 62, further comprising a sensing mechanism that senses whether the conductive surface area of the first or second electrode is to be placed on the patient.

64. The electrode arrangement of claim 62, further comprising an energy attenuator that causes the second electrode to transfer less electrical energy to the patient than the first electrode.

65. The electrode arrangement of claim 62, wherein the conductive surface area of the second electrode is smaller than the conductive surface area of the first electrode.

66. An electrode arrangement, comprising:

a first electrode disposed in a first plane and a second electrode disposed in a second plane that is other than the first plane, at least a portion of the first electrode overlying at least a portion of the second electrode, each of the first and second electrodes having a back formed of an electrically nonconductive substrate and a face that includes a conductive surface area adapted for placement on a patient, a nonconductive liner having opposing sides;

wherein the face of the first electrode is releasably attached to one side of the liner and the face of the second electrode is releasably attached to the opposing side of the liner;

wherein the conductive surface area of the second electrode is smaller than the conductive surface area of the first electrode;

wherein the conductive surface areas of the first and second electrodes are electrically connected to each other; and wherein if the electrical connection between the conductive surface areas of the first and second electrodes is broken, the conductive surface area of only one of the first or second electrodes is placed on the patient.

67. The electrode arrangement of claim 66, further comprising a sensing mechanism that senses whether the conductive surface area of the first or second electrode is to be placed on the patient.

68. A medical device, comprising:

(a) a plurality of electrode arrangements adapted for placement on a patient, each electrode arrangement comprising a first electrode disposed in a first plane and a second electrode disposed in a second plane other than the first plane, at least a portion of the first electrode overlying at least a portion of the second electrode, each of the first and second electrodes having a back formed of an electrically nonconductive substrate and a face that includes a conductive surface area adapted for placement on a patient, a nonconductive liner having opposing sides, wherein the face of the first electrode is releasably attached to one side of the liner and the face of the second electrode is releasably attached to the opposing side of the liner and wherein the conductive surface areas of the first and second electrodes are electrically connected to one other, and wherein for each electrode arrangement, if the electrical connection between the conductive surface areas is broken, the conductive surface area of only one of the first or second electrodes in the electrode arrangement is placed on the patient; and (b) circuitry in communication with the plurality of electrode arrangements, said circuitry being configured to transfer electrical energy to or receive electrical energy from the patient after at least one electrode in each of the electrode arrangements has been placed on the patient.

69. The medical device of claim 68, further comprising a sensing mechanism that senses which electrode in each electrode arrangement has been placed on the patient.

70. The medical device of claim 69, wherein the medical device is further configured to modify the electrical energy to be transferred to the patient based on which electrodes in the plurality of electrode arrangements have been placed on the patient.

71. The medical device of claim 69, wherein the medical device is further configured to modify a display of information to a user of the medical device based on which electrodes in the plurality of electrode arrangements have been placed on the patient.

72. The medical adevice of claim 69, wherein the medical device is further configured to modify the waveform of the electrical energy to be transferred to the patient based on which electrodes in the plurality of electrode arrangements have been placed on the patient.

73. The medical device of claim 69, wherein the medical device is further configured to modify the routing of electrical energy to the electrodes in the plurality of electrode arrangements based on which electrodes in the plurality of electrode arrangements have been placed on the patient.

74. The medical device of claim 68, wherein the first and second electrodes in each electrode arrangement are separable prior to placement on the patient.

75. The medical device of claim 74, wherein for each electrode arrangement, the medical device is further configured to electrically disconnect the second electrode from the first electrode if the first and second electrodes in the electrode arrangement are separated.

76. The medical device of claim 68, wherein for each electrode arrangement, the conductive surface area of the first electrode is smaller than the conductive surface area of the second electrode.

* * * * *

UNITED STATES PATENT AND TRADEMARK OFFICE
CERTIFICATE OF CORRECTION

PATENT NO.         : 6,965,799 B2                                                                Page 1 of 1
APPLICATION NO. : 10/094949
DATED              : November 15, 2005
INVENTOR(S)        : Richard C. Nova et al.

It is certified that error appears in the above-identified patent and that said Letters Patent is hereby corrected as shown below:

In column 3, line 34, delete "DESCRIPTION" and insert -- BRIEF DESCRIPTION --, therefor.

In column 14, line 19, in Claim 10, delete "that senses" and insert -- senses --, therefor.

In column 17, line 51, in Claim 42, delete "is a" and insert -- is of a --, therefor.

In column 18, line 20, in Claim 48, delete "area" and insert -- area of --, therefor.

In column 18, line 55, in Claim 53, delete "bean" and insert -- been --, therefor.

In column 19, line 9, in Claim 55, delete "patient; and" and insert -- patient if the patient is of a first size and only the second electrode in the electrode arrangement is placed on the patient if the patient is of a second size; and --, therefor.

In column 19, line 13-16, in Claim 55, delete "patient if the patient is of a first size and only the second electrode in the electrode arrangement is placed on the patient if the patient is of a second size." and insert -- patient, --, therefor.

In column 21, line 14, in Claim 72, delete "adevice" and insert -- device --, therefor.

Signed and Sealed this

Twenty-third Day of March, 2010

David J. Kappos
*Director of the United States Patent and Trademark Office*